United States Patent
Nonaka

(10) Patent No.: US 7,186,980 B2
(45) Date of Patent: Mar. 6, 2007

(54) RADIATION IMAGING APPARATUS

(75) Inventor: Hideki Nonaka, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/456,996

(22) Filed: Jul. 12, 2006

(65) Prior Publication Data

US 2006/0243910 A1  Nov. 2, 2006

Related U.S. Application Data

(63) Continuation of application No. 10/818,998, filed on Apr. 5, 2004, now Pat. No. 7,078,693.

(30) Foreign Application Priority Data

May 16, 2003  (JP)  ............... 2003-138914

(51) Int. Cl.
*G01T 1/00* (2006.01)
*H01L 27/146* (2006.01)

(52) U.S. Cl. ............... 250/336.1; 250/370.08; 250/370.09

(58) Field of Classification Search ............. 250/336.1, 250/370.08, 370.09
See application file for complete search history.

(56) References Cited

FOREIGN PATENT DOCUMENTS

JP  7-236093  *  9/1995
JP  2001-268440  *  9/2001

* cited by examiner

*Primary Examiner*—Constantine Hannaher
*Assistant Examiner*—Mindy Vu
(74) *Attorney, Agent, or Firm*—Morgan & Finnegan LLP

(57) ABSTRACT

To efficiently generate image data by using correction data. First offset data is obtained in advance for each of a plurality of imaging times, and is stored in a second image storage unit. The imaging time requested by a user is selected from the plurality of imaging times by a control unit, and an object is shot in the selected imaging time so as to store image data in a first image storage unit. A correction processing unit offset-corrects the image data by using first offset data corresponding to the selected imaging time and outputs first image data (preview image). In parallel with an output of the first image data, an imaging operation without irradiation is performed to have second offset data on approximately the same conditions as actual imaging obtained by the control unit, and the image data is offset-corrected by using the obtained second offset data so as to output second image data.

6 Claims, 3 Drawing Sheets

RADIATION IMAGING APPARATUS

The present application is a continuation of U.S. application Ser. No. 10/818,998, filed Apr. 5, 2004, now U.S. Pat. No. 7,078,693 the contents of which is hereby incorporated by reference in its entirety.

BACKGROUND OF THE INVENTION

1. Field of the Invention

The present invention relates to a radiation imaging apparatus, and in particular, to a radiation imaging apparatus for generating image data by using correction data.

2. Related Background Art

Various types of imaging apparatuses have been produced as in the past, such as those using Si single-crystal sensors represented by a CCD-type sensor and a MOS-type sensor and large-size sensors having imaging devices comprised of PIN-type sensors of hydrogenated amorphous silicon arranged one-dimensionally or two-dimensionally.

As for such imaging apparatuses, they are not only used to obtain visible optical images as represented by a digital camera and a digital copying machine, but also development thereof as radiation imaging apparatuses for converting a radiological image into an electrical signal is underway in conjunction with advance in nuclear development, radiation medical instruments or nondestructive inspections.

There are many cases where an S/N ratio of the aforementioned imaging apparatuses is two to three digits, and the S/N ratio exceeding that has not been demanded as in the past. It has the following reasons (1) and (2) for instance.

(1) There is no analog-digital (A/D) converter suited to digitizing an output of a high S/N ratio with high precision.

(2) A data amount after A/D conversion becomes such a large capacity that restrictions are put on a memory and communication, resulting in inferior usability.

In recent years, however, there is increasing necessity of the radiation imaging apparatus having a high S/N ratio of four to five digits because of improved performance of the A/D converters, enlarged capacity of the memory and the advance in high-speed communication technology.

Nevertheless, the aforementioned imaging apparatuses in the past cannot avoid reduction in the S/N ratio due to dark noise because of variations in production processes.

Thus, the following method is proposed, for instance, as a method for solving the problem of the reduction in the S/N ratio.

First, on factory shipment of the radiation imaging apparatus, the apparatus has correction data for correcting the noise caused by a dark current (hereafter, referred to as dark noise) stored in the memory. And when the radiation imaging apparatus is used in reality, an image data obtained by imaging an object is corrected by using the correction data in said memory.

However, such a method has the problem described below.

First, in the case where a user obtains the image of the object by using the radiation imaging apparatus, the user usually selects and sets an operating condition for the apparatus based on the object, circumstances thereof, purposes of the imaging and so on.

In this case, each component constituting the radiation imaging apparatus changes its characteristics according to temperature and so on. Therefore, the condition on actually performing the aforementioned imaging is different from the condition on obtaining the correction data (factory shipment), and the dark noise as a cause of the reduction in the S/N ratio is subtly different in conjunction with it.

For this reason, even if the image data obtained on the actual imaging is corrected by using the correction data, an error included in the image data is not completely corrected. In particular, as disclosed in Japanese Patent Application Laid-Open No. 2001-268440, even if a correction is made by preparing offset data (correction data) for each imaging time, no correction can be made as to the error due to a factor other than the imaging time such as temperature change.

As previously described, it is a serious problem that the condition on the actual imaging is different from the condition on obtaining the correction data when obtaining imaging data of the high S/N ratio.

Thus, as disclosed in Japanese Patent Application Laid-Open No. 2001-141832, or Japanese Patent Application Laid-Open Nos. H10-208016, H10-327317 and H11-151233 by the assignee hereof, there is a proposed method of performing the same operation as the actual imaging in close timing to the imaging and obtaining the correction data in order to obtain the image data of the high S/N ratio by obtaining the correction data on approximately the same condition as the actual imaging.

However, there is a possibility of losing imaging timing desired by the user for the sake of obtaining the correction data.

Thus, as for the aforementioned technology, the image data is output through a correction process after waiting until the correction data is obtained and both the image data and correction data are completely obtained. Therefore, it takes time from an instruction for the imaging provided by the user until an actual output of the (corrected) image data.

As the correction data is obtained on the same condition as the actual imaging, delay time until a data output increases in proportion to exposure time on the imaging.

SUMMARY OF THE INVENTION

Thus, as for a radiation imaging apparatus in the past, it is not possible to efficiently generate image data by using correction data, and so various countermeasures against it have been desired.

The present invention has been implemented in consideration of the above-mentioned problem, and an object thereof is to provide the radiation imaging apparatus for efficiently generating the image data by using the correction data, for instance.

The radiation imaging apparatus of the present invention has a radiation detecting unit for converting received radiation into the image data, a storage unit for storing a first correction data group corresponding to a plurality of imaging times of the radiation detecting unit respectively, a correction unit for correcting the image data based on the correction data, and a control unit for controlling the radiation detecting unit and the correction unit, where the control unit reads the first correction data corresponding to the imaging times of the radiation detecting unit from the storage unit, and controls the correction unit so as to correct the image data based on the first correction data and generate first image data.

Other objects, features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings which are incorporated in and constitute a part of the specification, illustrate embodiments of the invention and, together with the descriptions, serve to explain the principle of the invention.

DESCRIPTION OF THE PREFERRED EMBODIMENTS

First Embodiment

Figure 1:
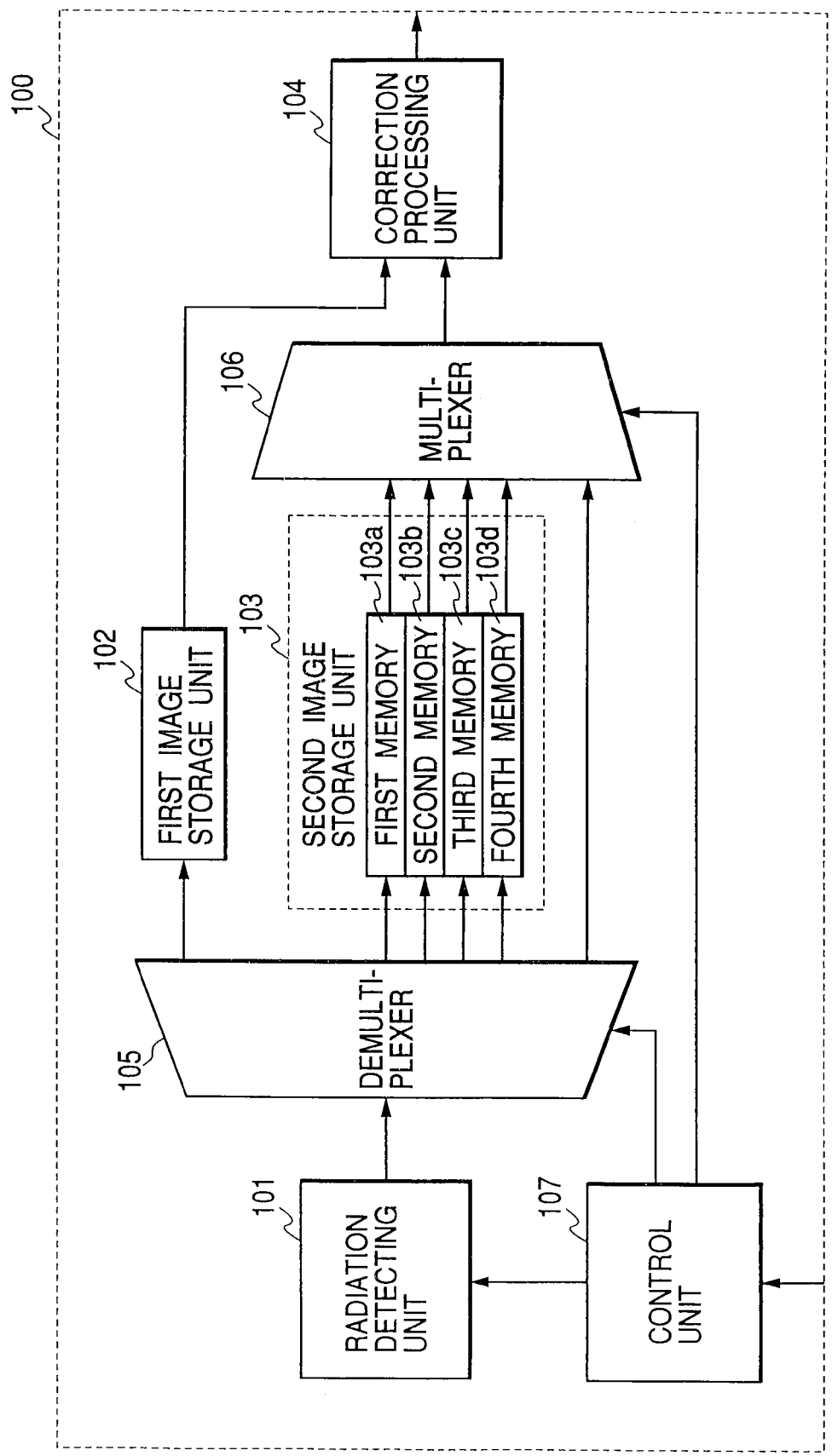
FIG. 1 is a block diagram showing a first embodiment of the present invention and showing an example of a configuration of a radiation imaging apparatus.

Next, a first embodiment of a radiation imaging apparatus of the present invention will be described by referring to the drawings.

According to this embodiment, a radiation imaging apparatus 100 as shown in FIG. 1 is used as an imaging apparatus for instance.

The radiation imaging apparatus 100 according to this embodiment is an apparatus for imaging a radiation (X-ray and so on) having passed through an object with an imaging device and thereby obtaining image data (digital radiation image data) of the object.

In particular, it has a configuration wherein first output image data (an image having undergone a tentative offset correction process) is output immediately after obtaining the image data, and second offset data is obtained approximately at the same time as this, and second output image data (the image having undergone a proper offset correction process) is transferred after obtaining the second offset data.

Thus, it has become possible to efficiently obtain the image data of a high S/N ratio and reduce delay time until outputting the image data compared with the past.

Hereafter, the configuration and operation of the radiation imaging apparatus 100 according to this embodiment will be concretely described.

Configuration of the Radiation Imaging Apparatus 100

As shown in the above-described FIG. 1, the radiation imaging apparatus 100 comprises radiation detecting unit 101, a first image storage unit 102, a second image storage unit 103 including a plurality of memories 103a to 103d, a correction processing unit 104, a demultiplexer 105, a multiplexer 106 and a control unit 107.

The radiation detecting unit 101 includes a scintillator, a photo-detector array, a drive circuit and an A/D converter though not shown.

In the radiation detecting unit 101, the scintillator has a matrix substance of a fluorescent material excited by a high-energy radiation having passed through the object so that fluorescence in a visible region can be obtained by recombination energy on a recombination.

This fluorescence is caused by a matrix itself of CaWO4, CdWO4 or the like or by a luminescence center substance added to the inside of the matrix of CsI:Tl, AnS:Ag or the like.

The photo-detector array is placed adjacently to the scintillator, and Outputs a photon by converting it into an electrical signal. The photo-detector array does not need to be limited in particular. For instance, it is possible to apply an element such as a solid imaging device (charge coupled device) or a photoelectron multiplier for instance. The configuration from the A/D converter onward does not change whatever element is used.

From the photo-detector array, a fluorescence amount detected in each pixel constituting the photo-detector array, that is, the electrical signal corresponding to a radiation amount incident on the fluorescent material of the scintillator is sequentially output by the operation of the drive circuit.

The A/D converter digitizes and outputs an output signal from the photo-detector array.

The first image storage unit 102 stores digital image data output from the radiation detecting unit 101 on an imaging operation.

The second image storage unit 103 stores first offset data for generating the first output image data. It is executed by performing the imaging operation without irradiation and having then the second image storage unit 103 store the digital image data output from the radiation detecting unit 101.

The correction processing unit 104 performs an offset correction process between the image data stored in the first image storage unit 102 and the first offset data output from the multiplexer 106 or the second offset data so as to output the image data having undergone this offset correction process.

The demultiplexer 105 selectively connects a data bus of the image data output from the radiation detecting unit 101 to the first image storage unit 102, the second image storage unit 103 or the multiplexer 106 by means of a control signal input from the control unit 107.

The multiplexer 106 selectively connects the data bus of the offset data from the second image storage unit 103 or the demultiplexer 105 to the correction processing unit 104 by means of the control signal input from the control unit 107.

The control unit 107 selects an imaging time according to a parameter input from the outside and controls the imaging operation of the radiation detecting unit 101, and also outputs a signal for switching the data bus according to the imaging operation, offset data obtaining operation and a difference in the imaging time to the demultiplexer 105 and the multiplexer 106.

Image Obtaining Operation of the Radiation Imaging Apparatus 100

Figure 2:
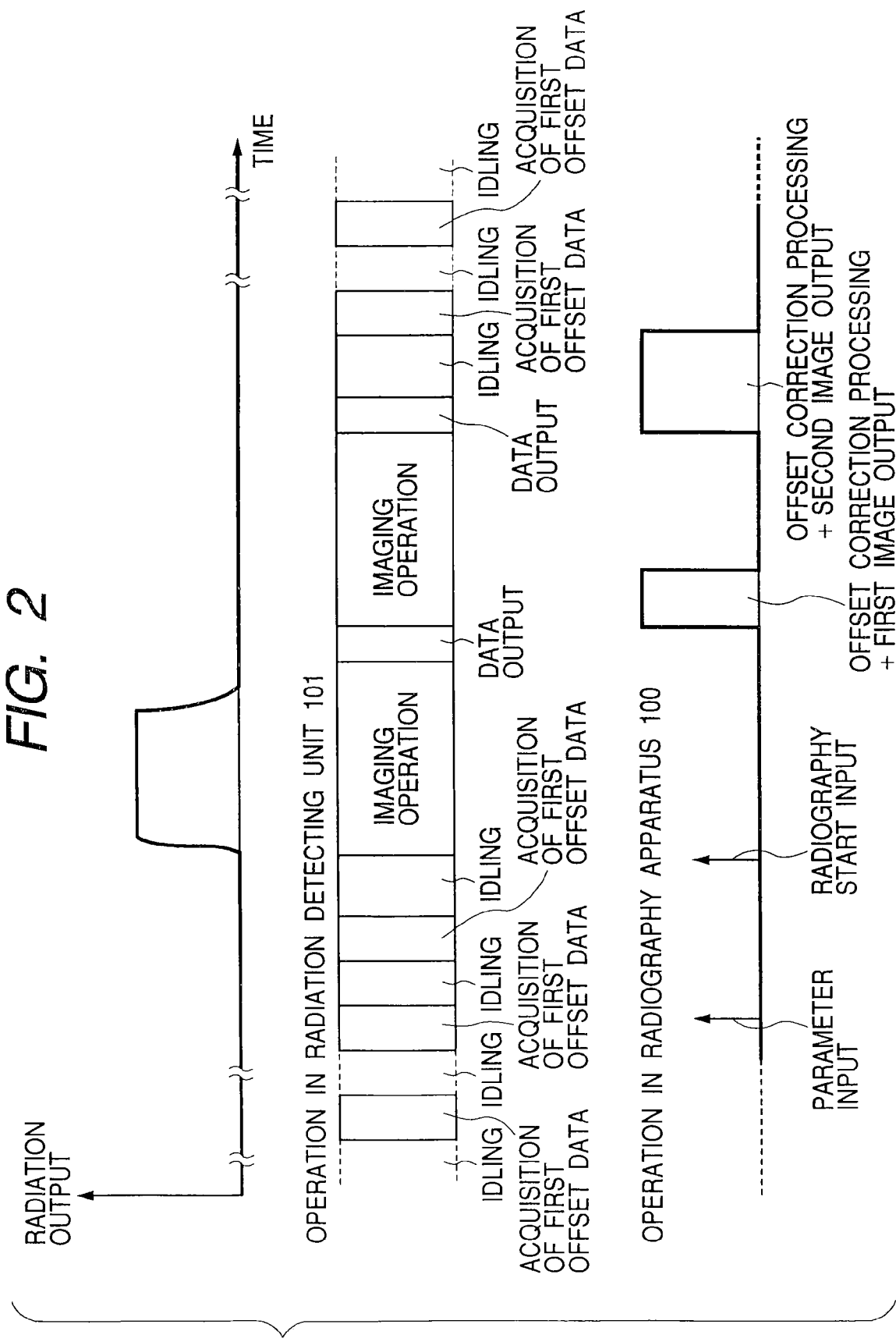
FIG. 2 is a time chart showing the first embodiment of the present invention and showing an example of a flow of operation of the radiation imaging apparatus.

Here, an actual image obtaining process using the radiation imaging apparatus 100 will be concretely described together with FIG. 2.

First, on imaging, the parameter is input to the control unit 107 by a user or an external input apparatus. Receiving this input, the imaging time in the radiation detecting unit 101 on an actual imaging operation is determined. In the case of the radiation imaging apparatus 100 according to this embodiment, several kinds of imaging time are prepared in advance, and a selection thereof is made so as to determine the actual imaging operation.

An offset error included in the image is mainly due to a dark current inherently possessed by the imaging device in the radiation detecting unit 101 and also due to a noise component (dark noise) which is mainly caused by a temperature drift of the electric components constituting the radiation detecting unit 101.

While the dark current as a dominant determiner of the offset error is different according to characteristics of the imaging device, there are the ones showing an almost steady-state value irrespective of the imaging time and the ones exponentially decreasing against the imaging time. The dark current in this case indicates an instantaneous value at a certain time, and so the obtained image data includes the offset error due to an integral amount in the imaging time of the dark current. To be more specific, the offset error increases in proportion to the imaging time. For this reason, in the case of the imaging times significantly different time-wise, the amount of the offset error contained in each of the obtained image data is different according to each imaging time in perspective. Therefore, it is not possible, in this case, to precisely correct the offset error with the same offset correction data.

To avoid this problem, there is also a method of always keeping the imaging time constant. In the case of assuming that the imaging time is one second, and if the actual time of irradiation is 10 milliseconds or so, a wasteful imaging operation without the incidence of the radiation which penetrated the object is performed for 990 milliseconds.

As previously described, the offset error increases in proportion to length of the imaging time, and so it poses a problem in terms of the S/N ratio. There is also a problem that a data output must wait until finishing accumulation even though the exposure itself has finished. The latter problem undermines instancy or real time operation as an advantage of a digital imaging apparatus, and is also a factor in reducing throughput of the apparatus.

Ideally, there is also a method of detecting an exposure state and moving on to a data output operation on finishing the exposure. However, it requires a dedicated exposure detecting unit separately in the case where this function cannot be implemented on the imaging device itself. For this reason, it leads to complication of the apparatus and increase in costs.

To render the radiation imaging apparatus 100 portable, it is necessary to render an apparatus shape low-profile and lightweight. To meet these demands, however, it is essential to use a flat panel imaging device (FPD) which does not require an optical system.

A PIN-type sensor using hydrogenated amorphous silicon which can be taken as a representative example of FPD uses glass as a base material, and has electronic circuits such as a photoelectric converter and a read gate circuit constituted thereon. Thus, the PIN-type sensor uses the glass which is a material brittle against an exogenous shock, and so a structural process is performed, such as sticking a reinforcing member separately for the sake of securing strength and distributing stress.

In the case of mounting the aforementioned exposure detecting unit, it needs to be mounted on the front or the back of the imaging device. In the case of mounting it on the front, there is a problem as to appearance of the exposure detecting unit on the image. In the case of mounting it on the back, it requires an action such as providing an opening to the aforementioned reinforcing member. It leads to reduction in mechanical strength and unevenness in back configuration of the imaging device. For this reason, there arise problems such as occurrence of a back scattering radiation and the appearance of the back configuration on the image. Regardless of whether mounting it on the front or on the back, an increase in apparatus weight and an increase in outline thickness are inevitable.

As a method for solving the above problems, this embodiment adopts a technique of limiting the imaging time to several kinds. Thus, the exposure detecting unit is no longer necessary, and the aforementioned machine structural problem is solved. It is also possible to select the imaging time according to the user's request rather than a uniquely determined imaging time so as to perform the imaging suited to an imaging subject (region) and solve the aforementioned problem in the case of always using the constant imaging time.

As previously mentioned, the offset error increases in proportion to the length of the imaging time, the offset data is required for each imaging time. It is possible to obtain the offset data before the actual imaging operation because the time of irradiation is limited to several kinds.

However, an operating condition on performing the actual imaging operation is different from that on obtaining the offset data, and so it is not possible to completely correct the offset error contained in the image data. As for the imaging time as a dominant determiner of the offset error amount, it is obtained on the same condition as the image data, and so it includes a profile of the entire offset error components. For this reason, the offset data obtained in advance (the first offset data) is used for an offset correction on the output of a first image data performed immediately after the imaging operation.

Here, the first image data to be output is equivalent to a so-called preview image for informing the user of an outline of current imaging results, and is intended to convey to the user the entire image rather than image quality itself. For that reason, it is not essential to output the entire image data, and the application is sufficiently satisfied by rendering a preview display 1/n (n: natural number) times an original image size. Therefore, the first image data may be output in a size which is 1/n (n: natural number) times the original image size accordingly.

As the first offset data is intended to correct the error caused by system noise possessed by the radiation detecting unit 101, it is obtainable by performing the imaging operation with no irradiation.

For this reason, as for the methods of obtaining the first offset data, there are the methods of obtaining it in spare time such as an interval between the imagings of the object, or immediately after activation such as switch-on or a reset of the radiation imaging apparatus 100 or on factory shipment, for instance.

In the case of the former two methods, the first offset data is updated each time it is obtained. As for the latter, it is wise not to update it because it is factory shipment data.

As a matter of course, the first offset data is obtained according to several kinds of imaging time set on the radiation imaging apparatus 100, and is stored in the first to fourth memories of the second image storage unit 103 under control of the demultiplexer 105 in accordance with the imaging time by the control unit 107. The first offset data is used for the preview image as previously described, and so it does not always need to hold the entire image data. Therefore, it is possible, by storing the data 1/n (n: natural number) times the original image size as the first offset data in accordance with the preview image size, to satisfy the application and reduce a capacity of the second image storage unit 103.

If an instruction to start imaging is provided by an imaging start button not shown at the instant when preparation of the first offset data and a setting of the imaging time are performed in advance, the radiation is irradiated to the object placed on the front of the radiation imaging apparatus 100 from a radiation source not shown.

If the radiation is irradiated to the object, the radiation is differently absorbed and scattered according to differences in constituents in the object. Consequently, the radiation incident on the radiation detecting unit 101 forms a transmission image depending on the configuration inside the object.

The radiation detecting unit 101 generates the digital image data from the incident radiation by means of the aforementioned image data output process. At this time, the control unit 107 controls the imaging time of the radiation detecting unit 101 according to the parameter given from the outside, and also controls the demultiplexer 105 to connect the output of the radiation detecting unit 101 to the first image storage unit 102. At the same time, the control unit 107 controls the multiplexer 106 to connect the second image storage unit 103 storing the first offset data corresponding to a set imaging time to the correction processing unit 104.

The output image data is stored by the first image storage unit 102 and sent to the correction processing unit 104, and undergoes the offset correction process between it and corresponding image data of the first offset data stored in the second image storage unit 103 so as to be output as the first image data to the outside thereafter.

The first offset data used for the offset correction at this time is the first offset data corresponding to the imaging time currently used for the imaging on the second image storage unit 103 selected by the multiplexer 106 as previously mentioned.

As previously mentioned, the first image data output at this time does not need to be the original image size but may also be a reduced size of 1/n (n: natural number) times.

In parallel with the output of the first image data, the imaging operation without the irradiation for obtaining the second offset data is performed. On completion of the output of the first image data, the control unit 107 controls the demultiplexer 105 to connect the output of the radiation detecting unit 101 to the multiplexer 106.

At the same time, the multiplexer 106 has the input controlled to connect the output from the demultiplexer 105 to the correction processing unit 104. This is the technique applied in the case where imaging operation time for obtaining the second offset data, that is, the imaging time determined by an externally input parameter is longer than the time required for outputting the first image data.

In the case where the condition is not satisfied, that is, in the case where the time required for outputting the first image data is longer than the imaging operation time for obtaining the second offset data, the second offset data disappears. As the technique for avoiding it, the method of rendering the selectable imaging time longer than the time required for outputting the first image data without fail is adopted.

On completion of the imaging operation without the irradiation for obtaining the second offset data, the second offset data is output from the radiation detecting unit 101. The image data stored in the first image storage unit 102 undergoes the offset correction process between it and corresponding image data of the output second offset data so as to be output as the second image data to the outside thereafter.

As described above, according to this embodiment, the imaging time is limited to several kinds, and the first offset data is obtained in advance for each limited imaging time so as to select the imaging time requested by the user from several kinds of imaging time on the imaging. The object is shot in the selected imaging time, and the shot image data is offset-corrected by using the first offset data corresponding to the selected imaging time so as to output it as the first image data.(preview image). And the imaging operation without the irradiation is performed in parallel with the output of the first image data, and the second offset data on approximately the same condition as the actual imaging is obtained so as to offset-correct the shot image data by using the obtained second offset data and output it as the second image data.

Thus, it is possible to perform the offset correction for obtaining the image data actually required by the user in parallel with the process for outputting the first image data (preview image) for informing the user of an outline of the current imaging results. Therefore, it is possible to efficiently obtain the image of the high S/N ratio. To be more specific, it is possible to reduce the delay time until displaying the image of the high S/N. ratio so as to provide the image of the high S/N ratio to the user without a sense of discomfort.

Second Embodiment

Next, a second embodiment of the present invention will be described.

This embodiment is different from the aforementioned first embodiment as to the method for avoiding the problem that the second offset data disappears in the case where the time required for outputting the first image data is longer than the imaging operation time for obtaining the second offset data. Therefore, a detailed description is omitted as to the same portions as the aforementioned first embodiment.

Figure 3:
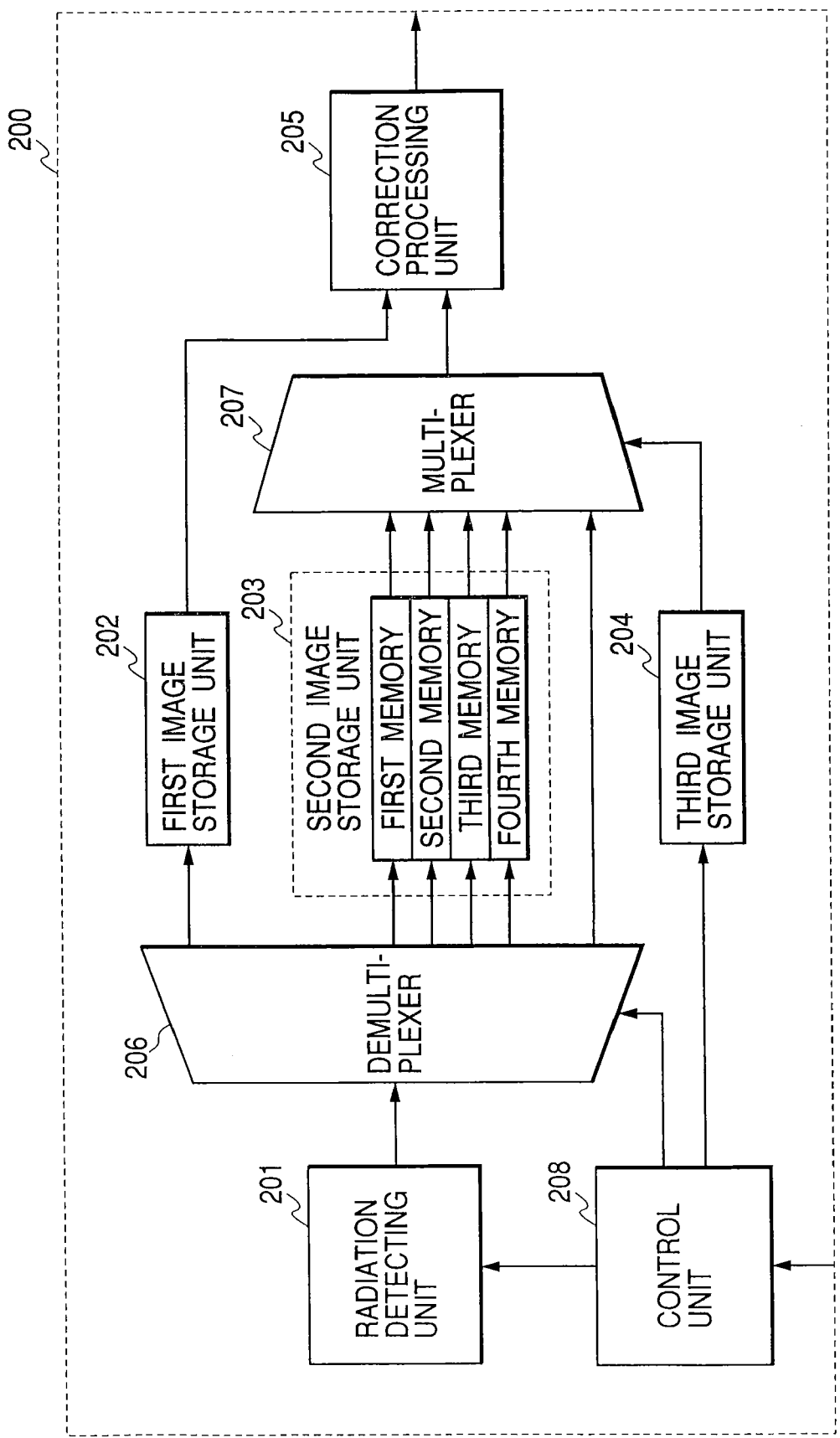
FIG. 3 is a block diagram showing a second embodiment of the present invention and showing an example of the configuration of the radiation imaging apparatus.

As shown in FIG. 3, a radiation imaging apparatus 200 according to this embodiment has a third image storage unit 204 provided between a demultiplexer 206 and a multiplexer 207, and the second offset data obtained as previously mentioned is stored in the third image storage unit 204.

This embodiment is not different from the aforementioned first embodiment as to the configuration up to the output of the first image data and roles and operations of the components. When the output of the first image data is started and the imaging operation for obtaining the second offset data is started almost at the same time, a control unit 208 connects the output of a radiation detecting unit 201 to the third image storage unit 204.

On completion of the imaging operation without the irradiation for obtaining the second offset data, the second offset data is output from the radiation detecting unit 201. The output second offset data is stored in the third image storage unit 204 via the demultiplexer 206.

Thus, even in the case where the output of the first image data is not completed on outputting the second offset data from the radiation detecting unit 201, disappearance of the second offset data can be avoided. And as a second image storage unit 203 is connected to a correction processing unit 205 via the multiplexer 207, the output of the first image data performed after undergoing the offset correction is not interrupted so as to perform both the operations in parallel.

And on completion of the output of the first image data, the control unit 208 controls the multiplexer 207 to connect the third image storage unit 204 to the correction processing unit 205. Thereafter, in the correction processing unit 205, the image data stored in the first image storage unit 202 undergoes the offset correction process between it and the corresponding image data of the second offset data stored in the third image storage unit 204 so as to be output as the second image data to the outside.

On this operation, it is also possible to store the second offset data of all the images in the third image storage unit 204 from the radiation detecting unit 201 and then start the operation for outputting the second image data. It is also possible to start the operation for outputting the second image data before completion of storage of all the images in the case where it is assured that, in each pixel constituting the image, timing for outputting the second offset data to the correction processing unit 205 is later than the timing for storing the second offset data in the third image storage unit 204 from the radiation detecting unit 201.

Another Embodiment of the Present Invention

The present invention also includes in its category an embodiment wherein, to operate various devices for the sake of implementing functions of the aforementioned embodiments, a software program code for implementing the functions of the embodiments is provided to a computer in the apparatus or system connected to the devices, and the devices are operated according to the program stored in the computer (a CPU or an MPU) of the system or apparatus.

In this case, the software program code itself implements the functions of the aforementioned embodiments, and the program code itself and means for providing the program code to the computer such as a recording medium storing such program code constitute the present invention. As for the recording medium for storing such program code, a flexible disk, a hard disk, an optical disk, a magnet-optical disk, a CD-ROM, a magnetic tape, a nonvolatile memory card or a ROM may be used.

It goes without saying that the program code is included in the embodiments of the present invention in the case where not only the functions of the aforementioned embodiments are implemented by having the provided program code executed by the computer, but also the functions are implemented by the program code in conjunction with an OS (Operating System) or other application software operating on the computer.

Furthermore, it goes without saying that the present invention includes the case where, after the provided program code is stored in a memory provided to a feature expansion board of the computer or a feature expansion unit connected to the computer, the CPU and so on provided to the feature expansion board or the feature expansion unit performs a part or all of actual processing based on instructions of the program code so as to thereby implement the functions of the aforementioned embodiments.

As for the radiation imaging apparatus according to the present invention, it is possible, as described above, to provide the radiation imaging apparatus for efficiently generating the image data by using the correction data.

The present invention is not limited to the above embodiments and various changes and modifications can be made within the spirit and scope of the present invention. Therefore to apprise the public of the scope of the present invention, the following claims are made.

What is claimed is:

1. A radiation image correcting apparatus for correcting image data from a radiation detecting unit for converting detected radiation into the image data, comprising:

a correction unit for performing a first offset correction of the image data to display corrected image data, based on a first correction data corresponding to imaging condition of the radiation detecting unit, wherein the first correction data is stored in a memory; and;

a controller for controlling the radiation detecting unit to obtain a second correction data to perform a second offset correction of the image data from the radiation detecting unit after having obtained the image data in parallel with performing an offset correction of the correction unit based on the first correction data.

2. The apparatus according to claim 1, wherein the radiation detecting unit is configured by a plurality of imaging elements and the first correction data and the second correction data are data for correcting a dark current of the plurality of imaging elements.

3. An apparatus according to claim 1, wherein the correction unit corrects the image data which is reduced by 1/n (n: natural number) by use of a correction data which is reduced by 1/n (n: natural number).

4. An apparatus according to claim 1, wherein the first correction data and the second correction data are produced based on an image data which is imaged under a condition where the radiation detecting unit doesn't receive radiation.

5. A radiation image correcting method for correcting image data from a radiation detecting unit for converting detected radiation into the image data, comprising:

a radiation detecting step for converting detected radiation into image data;

a first correction step for performing a first offset correction of the image data to display corrected image data, based on a first correction data corresponding to imaging condition of the radiation detecting unit, wherein the first correction data is stored in a memory;

a second correction data obtaining step for obtaining a second correction data from the radiation detecting unit after having obtained the image data in parallel with performing an offset correction based on the first correction data at the first correction step; and a second correction step for performing a second offset correction of the image data based on the second correction data.

6. A computer readable storage medium storing a control program for controlling a radiation image correcting apparatus which corrects image data from a radiation detecting unit for converting detected radiation into the image data, said control program comprising:

a program code for a radiation detecting step for converting detected radiation into image data;

a program code for a first correction step for performing a first offset correction of the image data to display corrected image data, based on the first correction data corresponding to imaging condition of the radiation detecting unit, wherein the first correction data is stored in a memory;

a program code for a second correction data obtaining step for obtaining a second correction data from the radiation detecting unit after having obtained the image data in parallel with performing an offset correction based on the first correction data at the first correction step; and a program code for a second correction step for performing a second offset correction of the image data based on the second correction data.

* * * * *